US00PP22828P2

(12) United States Plant Patent
Kordes

(10) Patent No.: US PP22,828 P2
(45) Date of Patent: Jul. 3, 2012

(54) FLORIBUNDA ROSE PLANT NAMED 'KORTUTU'

(50) Latin Name: *Rosa hybrida*
Varietal Denomination: KORtutu

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,240

(22) Filed: Oct. 14, 2010

(51) Int. Cl.
*A01H 5/00* (2006.01)

(52) U.S. Cl. ..... Plt./151

(58) Field of Classification Search ..... Plt./151, Plt./150, 140
See application file for complete search history.

*Primary Examiner* — June Hwu

(57) ABSTRACT

A new and distinct variety of rose with long lasting, novel dark red flowers, and attractive foliage with good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtutu'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2000. The crossing was between an unnamed seedling from the same breeder, and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtutu'.

SUMMARY OF THE INVENTION

The new rose plant may be distinguished from its seed parent, an unnamed seedling, by the following combination of characteristics:

1. Petal count for 'KORtutu' is double. Petal count for the seed parent is semi-double.
2. Flower diameter for 'KORtutu' is 100 mm on average. Flower diameter for the seed parent is 60 mm on average.

The new rose plant may be distinguished from its pollen parent, an unnamed seedling, by the following combination of characteristics:

1. 'KORtutu' reaches a height of 80 cm. The pollen parent reaches a height of 120 cm.
2. The common color of the flower bloom of 'KORtutu' is dark red. The common color of the flower bloom of the pollen parent is medium red.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORtutu' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtutu' was selected in May, 2001 from the seedling beds to be asexually propagated for further evaluation. The first asexual propagation of 'KORtutu' was done by budding to seedling understocks in July, 2001 at the inventor's nursery in Offenseth-Sparrieshoop, Germany.

This initial and other subsequent propagations conducted in controlled environments demonstrate that 'KORtutu' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORtutu'.

DETAILED BOTANICAL DESCRIPTION

The following is a description of 'KORtutu', as observed growing in October, 2010 in a nursery in Jackson County, Oreg. on plants of five years of age. Color references are made using The Royal Horticultural Society (London, England) Colour Chart, 2001 except where common terms of color are used.

For a comparison, several physical characteristics of the rose variety 'KORtocrea', an unpatented rose variety from the same inventor are compared to 'KORtutu' in Chart 1.

CHART 1

| Characteristic | 'KORtutu' | 'KORtocrea' |
|---|---|---|
| Average height of mature plant | 80 cm | 120-150 cm |
| Average flower diameter | 100 mm | 120 mm |
| Fragrance | Slight | Moderate |

Parents:

*Seed parent*.—An unnamed seedling.

*Pollen parent*.—An unnamed seedling.

Classification:

*Botanical classification*.—*Rosa hybrida*, 'KORtutu'.

*Commercial classification*.—Floribunda rose.

FLOWER AND FLOWER BUD

Blooming habit: Recurrent.

Flower bud:

*Size*.—Upon opening, 40 mm in length from base of receptacle to end of bud and 25 mm diameter at its widest point.

*Bud form*.—Long. Pointed ovoid.

*Bud color*.—As sepals first unfold, bud color is Gray-Purple Group 187B. When ¼ open, the upper surface of petals is Red Group 46B, and the lower surface is Gray-Purple Group 185A.

*Sepals*.—Size: Average 40 mm long×10 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Covered in fine hairs. Outer surface: Glabrous. Stipitate glands are absent. Color: Upper surface Yellow-Green Group 146A. Lower surface Yellow-Green Group 146B.

Receptacle:

*Surface*.—Smooth. With stipitate glands.

*Color*.—Yellow-Green Group 144A. Intonations of Gray-Red Group 182A.

*Shape*.—Campanulate.

*Size*.—12 mm (h)×15 mm (w).

Peduncle:

*Surface*.—Smooth.

*Length*.—60-75 mm average length.

*Diameter*.—4 mm average diameter.

*Color*.—Yellow-Green Group 144A. Intonations of Gray-Red Group 182A.

*Strength*.—Strong.

*Borne*.—Singly.

Flower bloom:

*Fragrance*.—Light.

*Duration*.—On the plant 7-9 days. As a cut flower, 4 to 6 days. Senesced petals drop away cleanly.

*Size*.—Large flowered garden rose. When open, the average flower diameter is 100 mm and the average flower height is 55 mm.

*Form*.—Shape of flower when viewed from the side: Upon opening, upper part: Flattened convex. Upon opening, lower part: Flat. Open flower, upper part: Cupped. Open flower, lower part: Flat.

Color:

*Upon opening, petals*.—Outermost petals: Outer Side: Red Group 46A. Inner Side: Red Group 46A. Innermost petals: Outer Side: Red Group 46A. Inner Side: Red Group 45A.

*Upon opening, basal petal spots*.—Basal petal spot, outermost petals: Outer Side: Yellow Group 10C. Inner Side: Yellow Group 10A. Basal petal spot, innermost petals: Outer Side: Yellow Group 9B. Inner Side: Yellow Group 9A.

*After opening, petals*.—Outermost petals: Outer Side: Red Group 46A. Inner Side: Red Group 46B. Innermost petals: Outer Side: Red Group 46A. Inner Side: Red Group 45A.

*After opening, basal petal spots*.—Basal petal spot, outermost petals: Outer Side: Yellow Group 10C. Inner Side: Yellow Group 10A. Basal petal spot, innermost petals: Outer Side: Yellow Group 9B. Inner Side: Yellow Group 9A. Variegations: Occasional streak of White Group 155D on the innermost petals.

General tonality: On open flower Red Group 46A. No change in the general tonality at the end of the $9^{th}$ day. Afterwards, general tonality is Red Group 53A.

Petals:

*Petal count*.—Approximately 42-48 petals under normal conditions.

*Petal reflex*.—Petals reflex slightly.

*Petal edge*.—Entire.

*Petal shape*.—Round. Apex shape is round. Shape of base is rounded.

*Petal size*.—40-45 mm long; 40-45 mm wide.

*Thickness*.—Average.

*Petal arrangement*.—Generally in a regular pattern with overlapping edges.

Petaloids: Present.

*Petaloid count*.—Average of 4-8 per flower.

*Petaloid edge*.—Smooth.

*Petaloid texture*.—Smooth.

*Petaloid shape*.—Linear to elliptic.

*Petaloid size*.—Petaloids are 12 mm long and 8 mm wide.

*Petaloid color*.—Color of inner side is Red Group 46A. Color of outer side is Red Group 46A.

Reproductive organs:

*Pistils*.—Approximately 80-100 present. Stigmas: Location: Inferior in position to anthers. Color: Gray-Yellow Group 160A. Styles: Length: 10 mm long. Color: Gray-Yellow Group 160A.

*Stamens*.—Approximately 60-80 on average and regularly arranged. Anthers: Size: 2-3 mm long. Color: Gray-Orange Group 173C. Pollen: Generally absent. Filaments: Color: Yellow Group 8A. Intonations of Red Group 40B. Length: 14 mm.

THE PLANT

Plant growth: Moderate vigor. Upright to bushy habit. When grown as a budded nursery plant the average plant height is 80 cm and the average plant width is 60 cm.

Stems:

*Stem color*.—Young wood: Yellow-Green Group 144A. Older wood: Yellow-Green Group 144A.

*Stem surface*.—Young wood: Smooth. Older wood: Smooth.

Prickles: Present.

*Incidence*.—12-18 per 10 cm of juvenile stem; 6-10 per 10 cm of mature stem.

*Size*.—Average length: 8 mm.

*Color*.—Immature prickles: Gray-Purple Group 185A. Mature prickles: Gray-Red Group 182A. Senescing to Gray-Orange Group 174A.

*Shape*.—Concave.

Leaves and leaflets: Normally 5-7 leaflets on normal leaves in middle of the stem.

*Venation pattern*.—Pyramidal net pattern.

*Leaf size*.—125 mm (l)×90 mm (w).

*Quantity*.—Abundant.

*Texture*.—Upper side of leaflet: Semi glossy. Smooth. Leathery. Under side of leaflet: Matte. Smooth. Leathery.

*Color, mature foliage*.—Upper Leaf Surface: Green Group 137A. Lower Leaf Surface: Yellow-Green Group 146B.

*Color, juvenile foliage*.—Upper Leaf Surface: Green Group 137A. Lower Leaf Surface: Yellow-Green Group 146B.

*Anthocyanin intonation*.—Present. Location: Intonations present on juvenile leaf margins and developing leaves. Color: Gray-Purple Group 183B.

Stipules:

*Size*.—20 mm long. 7 mm between the tips of the stipule. Main body of stipule 2 mm in width.

*Shape*.—Elongated; winged along middle.

*Stipule color*.—Yellow-Green Group 146B.

*Presence of stipitate glands*.—Generally lacking.

*Margins*.—Serrated.

Petiole:

*Length*.—30 mm.

*Diameter*.—1.5 mm.

*Petiole color*.—Yellow-Green Group 144A.

*Underneath*.—A few small prickles underneath.

*Stipitate glands*.—Limited numbers of stipitate glands on margins.

Petiole rachis:

*Length*.—40 mm.

*Diameter*.—1 mm.

*Color*.—Yellow-Green Group 144A. Anthocyanin present on juvenile tissue. Color: Gray-Purple Group 185A.

*Margins*.—Smooth.

*Prickles*.—A few small prickles underneath.

*Stipitate glands*.—Limited numbers of stipitate glands on margins.

Leaflets:

*Size*.—Average size of the terminal leaflet is 45-50 mm (l)×35-40 mm (w).

*Shape*.—Broadly ovate. Base: Ovate. Apex: Acute.

*Margins*.—Serrated.

*Texture*.—Leathery.

Hips/seed formation: None observed.

Winter hardiness: To date, the variety has been grown successfully in Zone 5.

Disease resistance: Above average resistance to Powdery mildew (*Sphaerotheca pannosa*), rust (*Phragmidium* spp.), and blackspot (*Diplocarpon rosae*) diseases under normal growing conditions.

I claim:

1. A new and distinct variety of rose plant, as described and illustrated herein.

* * * * *

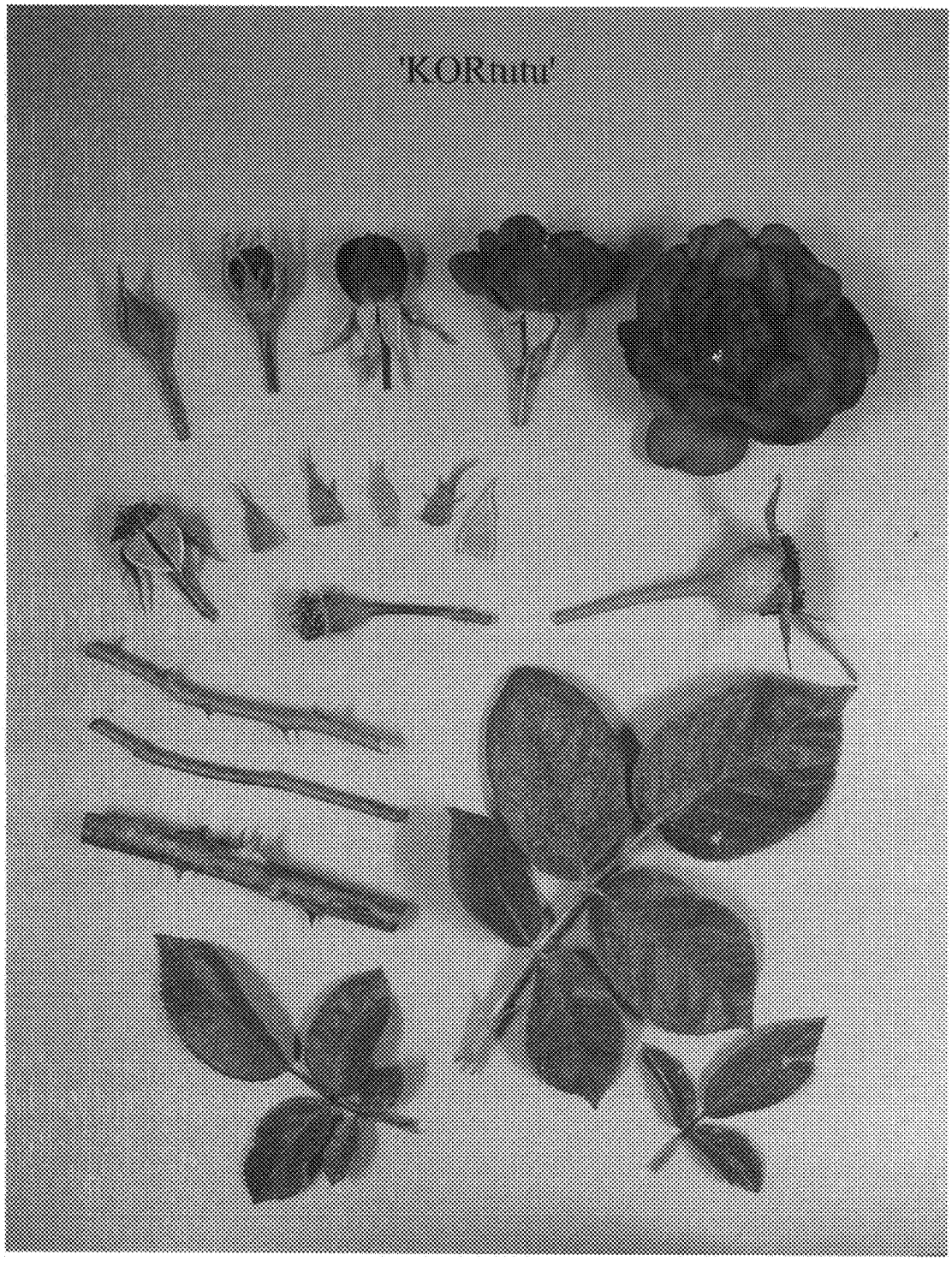
'KORnitu'